United States Patent
Jiang et al.

(10) Patent No.: US 9,643,975 B2
(45) Date of Patent: May 9, 2017

(54) SYNTHESIS METHOD OF 9-ALLYLCAMPTOTHECIN DERIVATIVES

(71) Applicant: SHANGHAI HAIHE PHARMACEUTICAL CO., LTD., Shanghai (CN)

(72) Inventors: Lei Jiang, Shanghai (CN); Lei Liu, Shanghai (CN); Lei Li, Shanghai (CN)

(73) Assignee: SHANGHAI HAIHE PHARMACEUTICAL CO., LTD, Shanghai (CN)

( * ) Notice: Subject to any disclaimer, the term of this patent is extended or adjusted under 35 U.S.C. 154(b) by 0 days.

(21) Appl. No.: 15/111,452

(22) PCT Filed: Dec. 31, 2014

(86) PCT No.: PCT/CN2014/096002
§ 371 (c)(1),
(2) Date: Jul. 13, 2016

(87) PCT Pub. No.: WO2015/106633
PCT Pub. Date: Jul. 23, 2015

(65) Prior Publication Data
US 2016/0340364 A1    Nov. 24, 2016

(30) Foreign Application Priority Data

Jan. 15, 2014  (CN) .......................... 2014 1 0018451

(51) Int. Cl.
*C07D 491/22*  (2006.01)

(52) U.S. Cl.
CPC .................. *C07D 491/22* (2013.01)

(58) Field of Classification Search
CPC ..................................... C07D 491/22
USPC ........................................... 546/48
See application file for complete search history.

(56) References Cited

U.S. PATENT DOCUMENTS

| 8,299,251 B2 | 10/2012 | Toyoda et al. |
| 8,685,997 B2 * | 4/2014 | Lu ........................ C07D 491/22 514/283 |
| 8,865,997 B2 | 10/2014 | Hsu et al. |

FOREIGN PATENT DOCUMENTS

| CN | 101337966 A | 1/2009 |
| CN | 101880285 A | 11/2010 |
| CN | 102046634 A | 5/2011 |
| CN | 102627653 A | 8/2012 |
| WO | 2005044821 A1 | 5/2005 |
| WO | 2007104214 A1 | 9/2007 |

OTHER PUBLICATIONS

English translation International Search Report corresponding to PCT/CN2014/096002 mailed Mar. 23, 2015, 3 pages.

* cited by examiner

*Primary Examiner* — Patricia L Morris
(74) *Attorney, Agent, or Firm* — Mintz, Levin, Cohn, Ferris, Glovsky and Popeo, P.C.

(57) ABSTRACT

A method for preparing 9-allylcamptothecin derivatives using compound 14 as an essential intermediate. The total yield of the method is high.

12 Claims, No Drawings

SYNTHESIS METHOD OF 9-ALLYLCAMPTOTHECIN DERIVATIVES

FIELD OF THE INVENTION

The present invention belongs to pharmaceutical synthesis field. Specifically, the present invention relates to a synthesis method of 9-allylcamptothecin derivatives (Ximingtecan hydrochloride, compound 1H).

BACKGROUND OF THE INVENTION

In 2007, Shanghai Institute of Material Medica, Chinese Academy of Sciences, has carried out a series of modifications at the 9th site of camptothecin nucleus based on the 10-hydroxy camptothecin, (WO2005044821, WO2007104214), and finally found that 9-allyl-10-hydroxy-camptothecin (Jimmytecan, compound 6), among others, has shown an excellent anti-tumor activity in evaluation in vivo and in vitro. The water-soluble prodrug of the above, Ximingtecan hydrochloride (Compound 1H) has been subject to a thorough evaluation, and clinical trials has been applied from CFDA in October 2010, and clinical trial approval document has been obtained in May 2012, which is a promising candidate as anticancer drugs.

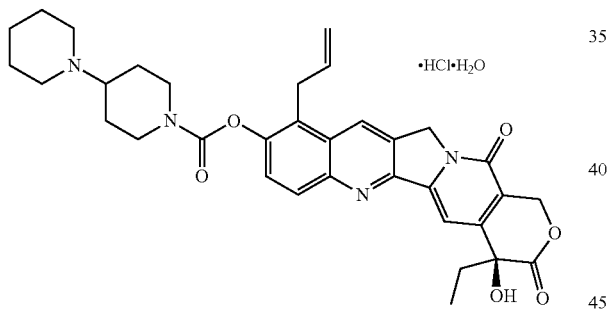

1H
·HCl·H₂O

At present, the main synthetic method of Ximingtecan hydrochloride is condensation of 9-allyl-10-hydroxycamptothecin (compound 6) and piperidinyl piperidine chloride chloroformate (Compound 7).

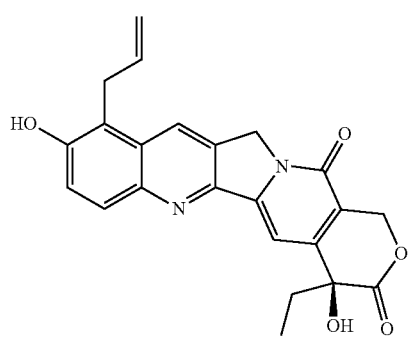

6

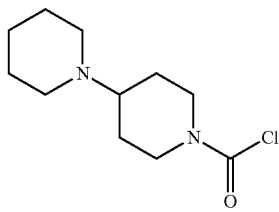

7

In which there are mainly two synthetics methods for compound 6.

In one method, 10-hydroxy camptothecin is used as raw material, and the product is obtained through two steps of reaction, alkylation and Claisen Rearrangement (WO2005044821), and the route of the method is shown as follows:

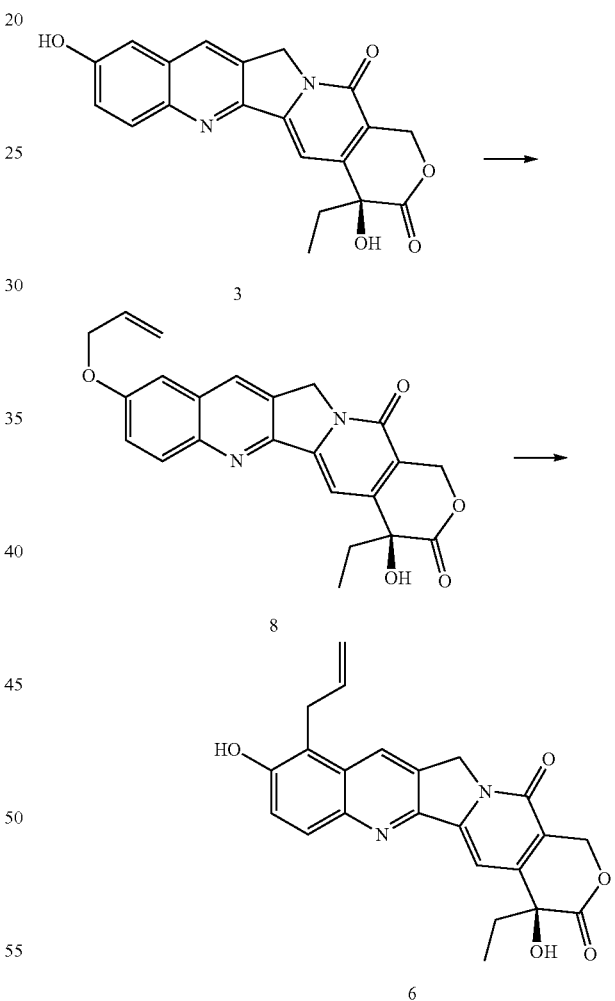

This synthetic route is adopted in the pilot scale production at present. However, there are obvious demerits for this route: firstly, an isomer impurity which was rearranged at 11th site would be produced during rearrangement process (compound 9). This compound is difficult to be completely removed even if column chromatography is used; secondly, the duration of rearrangement reaction is up to 72 hours, and the compound 8 can not be completely converted to compound 6, and there are still large amount of compound 8 present in the reaction system when the reaction is stopped. Since the product is similar to the impurity in structure, overall yield is significantly lower and separation and purification of the product are difficult. In actual operation, we found that it is difficult to obtain compound 6 of purity over 95%; therefore, repeated recrystallization is necessary for the purification of the final product 1H, thereby further reducing the yield. The overall yield of this route is about 16-20% at present.

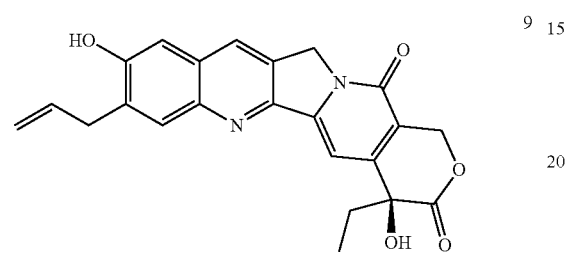

Another method to synthesize compound 6 reported in the literature is using metal palladium-catalyzed coupling reactions (Suzuki or Stille coupling) to give Compound 6 (CN101880285); the reaction route is as follows:

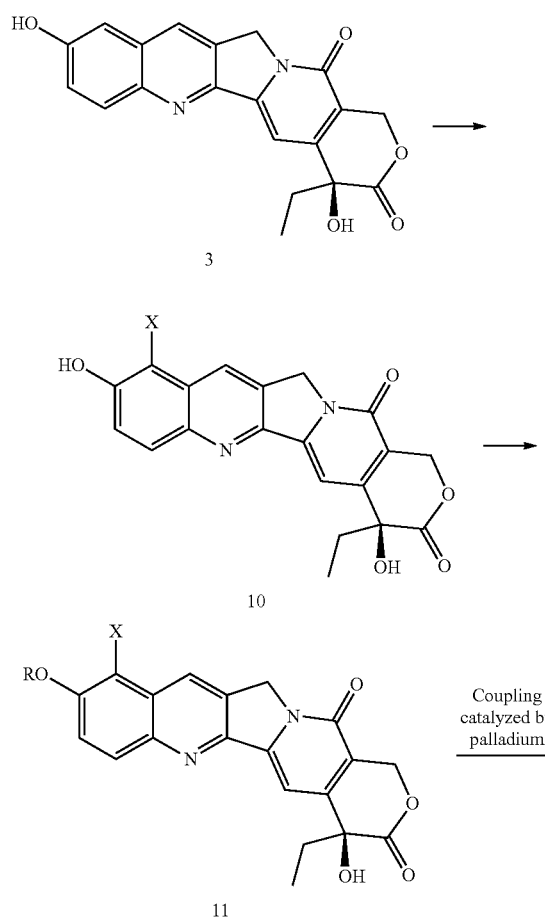

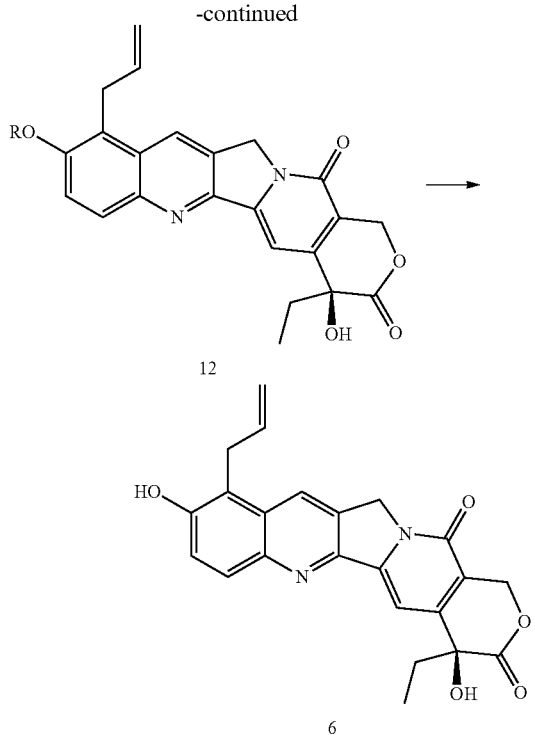

wherein X is Cl, Br or I, R is commonly used protecting group, particularly methoxymethyl, acetyl, ethoxycarbonyl, etc.

Although compound 6 of higher purity can be obtained and rearrangement isomer 9 can be avoided through the route, there are still significant problems: firstly, if Stille coupling was employed, highly toxic tin reagents are needed, use of which should be avoided in the production of drug; secondly, regarding to Suzuki coupling, compared with the previous synthetic route, there are two more steps during the reaction, while the overall yield was not significantly increased, which resulting the increase of labor and operating costs; thirdly, the palladium catalyst used in the reaction was of low activity, which make it impossible to achieve good yield; finally, there are two steps in the reaction involving chromatography purification, which will increase the complexity of operation and production costs. This route has not been used in the actual production.

Therefore, it will be of great significancy for the industrial production of medicaments in the future to develop a synthesis process for compound 1, which is of high efficiency, low cost, easy-amplification, and good repeatability.

SUMMARY OF THE INVENTION

The object of the present invention is to provide a synthesis method for 10-((4'-piperidinyl piperidine)carbonyloxy)-9-allyl-camptothecin hydrochloride monohydrate (compound 1), which is of good selectivity, high purity, and high overall yield. Using this method, the yield can be significantly improved, the production costs can be reduced, and time can be saved, thereby directly obtaining API of high-purity for clinical use.

In the first aspect of the present invention, a compound of formula 14 is provided,

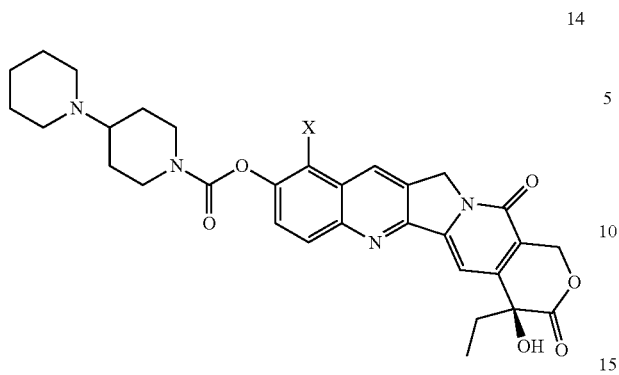

wherein X is halogen.

In another preferred embodiment, the halogen is chlorine, bromine or iodine.

In the second aspect of the present invention, a preparation method for compound 14 is provided, comprising the step: in an inert solvent, reacting compound 13 with compound 7 to give compound 14;

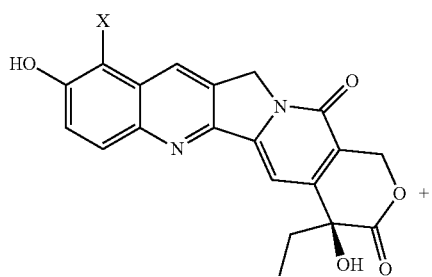

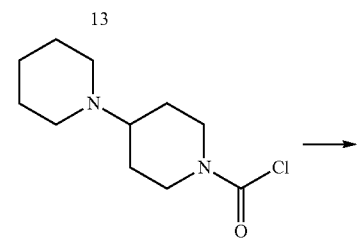

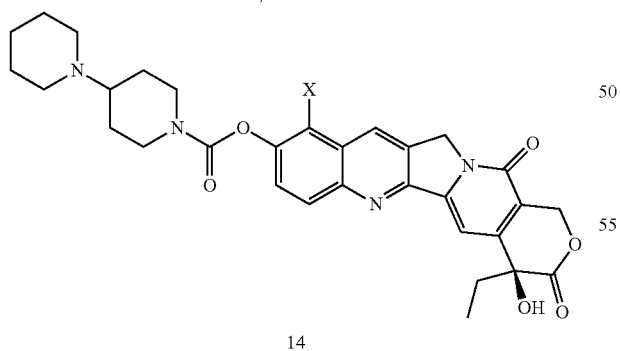

wherein in the above formulas, X is halogen.

In another preferred embodiment, compound 13 is prepared by a method comprising the following steps:

In an inert solvent, reacting compound 3 with a halogenating agent to give compound 13;

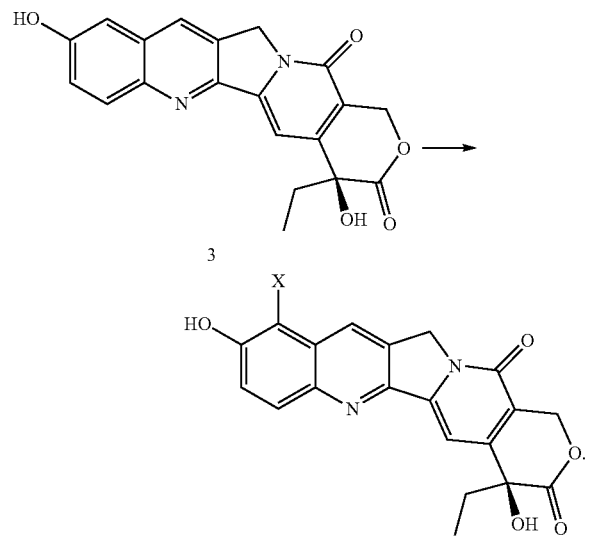

In another preferred embodiment, the halogenating agent is selected from the following group: bromine, iodine, iodine chloride, N-bromosuccinimide (NBS), N-iodosuccinimide (NIS), bromine chloride, 1,3-dibromo-1,3,5-triazine-2,4,6-trione.

In the third aspect of the present invention, a preparation method for compound 1 is provided, comprising a step: conducting Suzuki reaction to compound 14 and an allyl boron reagent to give compound 1;

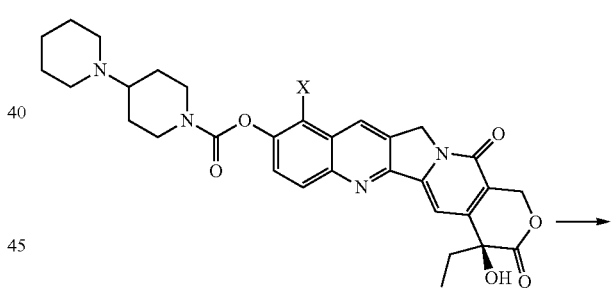

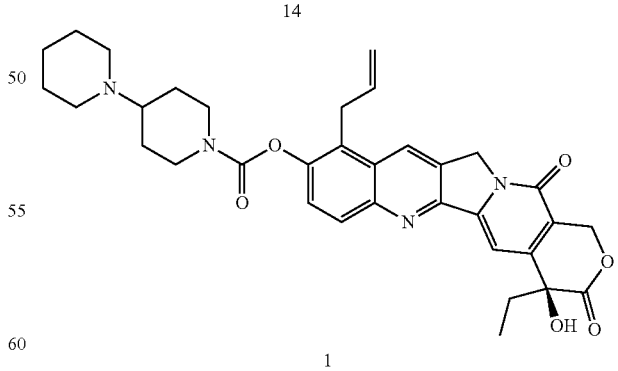

wherein in the above formulas, X is a halogen.

In another preferred embodiment, the allyl boron reagent is selected from the group consisting of: allylboronic acid pinacol ester, allyl boron fluoride complex salt.

In another preferred embodiment, the allyl boron fluoride complex salt is selected from the following group: the complex salt of allyl boron trifluoride and potassium fluoride.

In another preferred embodiment, compound 14 is prepared by the method of the second aspect of the present invention.

In another preferred embodiment, the Suzuki reaction was conducted in a system comprising following agents: palladium catalyst, phosphine ligand, alkali and inert solvent.

In another preferred embodiment,

The palladium catalyst is selected from the group consisting of: tris (dibenzylideneacetone) dipalladium ($Pd_2(dba)_3$), tetrakis (triphenylphosphine) palladium ($Pd(PPh_3)_4$), palladium acetate, dichlorobis (triphenylphosphine) palladium, palladium trifluoroacetate, triphenylphosphine palladium acetate, bis (tri-o-benzyl phosphine) palladium dichloride, 1,2-bis (diphenylphosphino) ethane dichloride palladium or combinations thereof;

The phosphine ligand is selected from the following group: tri-tert-butylphosphine, tri-tert-butylphosphine tetrafluoroborate, tri-n-butylphosphine, triphenylphosphine, tri-p-benzyl phosphine, tricyclohexylphosphine, tri-o-benzyl phosphine, or combinations thereof; the base is selected from the following group: potassium fluoride, cesium fluoride, hydrated potassium phosphate, potassium carbonate, sodium carbonate, sodium hydrogencarbonate, 1,8-diazabicyclo[5.4.0]undec-7-ene, triethylamine, diisopropylethylamine, pyridine or combinations thereof;

The inert solvent is selected from the following group: 1,4-dioxane, tetrahydrofuran, acetonitrile, dimethylsulfoxide, N, N-dimethylformamide, toluene, methanol, ethanol, isopropanol, n-butanol, tert-butanol, iso-butanol, benzyl alcohol, water or combinations thereof.

In another preferred embodiment, the palladium catalyst is selected from the group consisting of: tris (dibenzylideneacetone) dipalladium ($Pd_2(dba)_3$), tetrakis (triphenylphosphine) palladium ($Pd(PPh_3)_4$), or combinations thereof; and/ or The phosphine ligand is selected from the following group: tri-tert-butylphosphine, tri-tert-butylphosphine tetrafluoroborate, or combinations thereof; the base is selected from the following group: potassium fluoride, cesium fluoride, hydrated potassium phosphate, diisopropylethylamine, triethylamine, or combinations thereof;

The inert solvent is selected from the following group: 1,4-dioxane, isopropanol, water, benzyl alcohol, or combinations thereof.

In another preferred embodiment, the Suzuki reaction is conducted in a system selected from the following group:

(1) tris (dibenzylideneacetone) dipalladium, potassium fluoride, tri-tert-butylphosphine and 1,4-dioxane;

(2) tris (dibenzylideneacetone) dipalladium, tri-tert-butylphosphine, hydrated potassium phosphate and 1,4-dioxane;

(3) tris (dibenzylideneacetone) dipalladium, tri-tert-butylphosphine, potassium carbonate and 1,4-dioxane;

(4) tris (dibenzylideneacetone) dipalladium, tri-tert-butylphosphine, hydrated potassium phosphate, potassium fluoride and 1,4-dioxane;

(5) tris (dibenzylideneacetone) dipalladium, tri-tert-butylphosphine, diisopropylethylamine, potassium fluoride and 1,4-dioxane;

(6) tris (dibenzylideneacetone) dipalladium, tri-tert-butylphosphine, diisopropylethylamine, cesium fluoride and 1,4-dioxane;

(7) tris (dibenzylideneacetone) dipalladium, tri-tert-butylphosphine, triethylamine, potassium fluoride and 1,4-dioxane;

(8) tris (dibenzylideneacetone) dipalladium, tri-tert-butylphosphine, triethylamine, potassium fluoride and tetrahydrofuran;

(9) tetrakis (triphenylphosphine) palladium, tri-tert-butylphosphine, potassium fluoride and 1,4-dioxane;

(10) palladium acetate, tri-tert-butylphosphine, potassium fluoride and 1,4-dioxane;

(11) dichlorobis (triphenylphosphine) palladium, tri-tert-butylphosphine, potassium fluoride and 1,4-dioxane;

(12) tris (dibenzylideneacetone) dipalladium, tri-tert-butylphosphine, triethylamine, potassium fluoride and methanol;

(13) tris (dibenzylideneacetone) dipalladium, tri-tert-butylphosphine, diisopropylethylamine, potassium fluoride and methanol;

(14) tris (dibenzylideneacetone) dipalladium, tri-tert-butylphosphine, diisopropylethylamine and methanol;

(15) tetrakis (triphenylphosphine) palladium, tri-tert-butylphosphine, diisopropylethylamine and methanol;

(16) dichlorobis (triphenylphosphine) palladium, tri-tert-butylphosphine, diisopropylethylamine and methanol;

(17) tris (dibenzylideneacetone) dipalladium, triphenylphosphine, diisopropylethylamine, potassium fluoride and isopropanol;

(18) tris (dibenzylideneacetone) dipalladium, tri-tert-butylphosphine tetrafluoroborate, diisopropylethylamine and isopropanol;

(19) tris (dibenzylideneacetone) dipalladium, tri-tert-butylphosphine, diisopropylethylamine, potassium fluoride, water and isopropanol;

(20) tris (dibenzylideneacetone) dipalladium, tri-tert-butylphosphine, diisopropylethylamine, potassium fluoride, water and n-butyl alcohol;

(21) dichlorobis (triphenylphosphine) palladium, tri-tert-butylphosphine, diisopropylethylamine, water and n-butyl alcohol;

(22) tris (dibenzylideneacetone) dipalladium, tri-tert-butylphosphine, diisopropylethylamine, potassium fluoride and n-butyl alcohol;

(23) tris (dibenzylideneacetone) dipalladium, tri-tert-butylphosphine, diisopropylethylamine and n-butyl alcohol;

(24) tris (dibenzylideneacetone) dipalladium, potassium fluoride, tri-tert-butylphosphine tetrafluoroborate, diisopropylethylamine, 1,4-dioxane and water;

(25) tris (dibenzylideneacetone) dipalladium, potassium fluoride, tri-tert-butylphosphine tetrafluoroborate, diisopropylethylamine, 1,4-dioxane and water;

(26) tris (dibenzylideneacetone) dipalladium, potassium fluoride, tri-tert-butylphosphine tetrafluoroborate, diisopropylethylamine, isopropanol and water;

In another preferred embodiment, the method further comprises a step of: acidifying compound 1 to give compound 1H.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Through research, the inventor has unexpectedly discovered a method for the preparation of an intermediate for preparing 10-((4'-piperidinyl piperidine) carbonyloxy)-9-allyl-camptothecin hydrochloride monohydrate (compound 1) and for the preparation of compound 1. The method is of good selectivity, high purity, and significantly improved total yield, thus greatly reducing the cost of production, saving time, and directly obtaining high-purity drug for clinical use. The inventor has completed the present invention based on the above discoveries.

A preparation method for compound 1 is provide in the present invention, wherein 10-hydroxy camptothecin (compound 3) is used as a raw material, compound 1 is obtained by three steps of halogenations, coupling and Suzuki reaction, and the method comprises following steps:

(1) In an inert solvent (e.g., DMF, $CCl_4$, chloroform, acetic acid, etc), at a certain temperature (for example, $-20°$ C. to $50°$ C.), compound 3 was halogenated with a halogenating agent for a certain time (e.g., 0.5 to 6 hours), thus obtaining compound 13; wherein X is a halogen (e.g., chlorine, bromine, iodine);

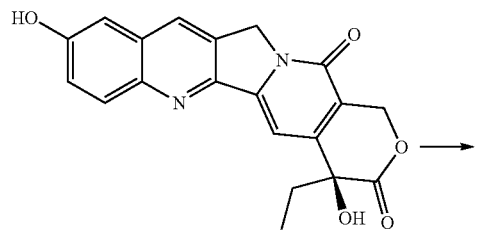

3

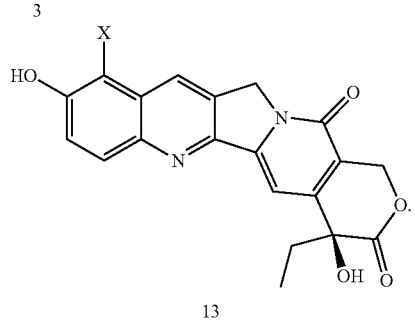

13 wherein the halogenating agent is selected from the following group: bromine, iodine, iodine chloride, N-bromosuccinimide (NBS), N-iodosuccinimide (NIS), bromine chloride, 1,3-dibromo-1,3,5-triazine-2,4,6-trione.

(2) In an inert solvent (e.g., dichloromethane, pyridine, tetrahydrofuran, etc), at a certain temperature (for example, $-20°$ C. to $25°$ C.), compound 13 is reacted with compound 7 for a certain time (e.g., 0.5 to 3 hours), thus obtaining compound 14;

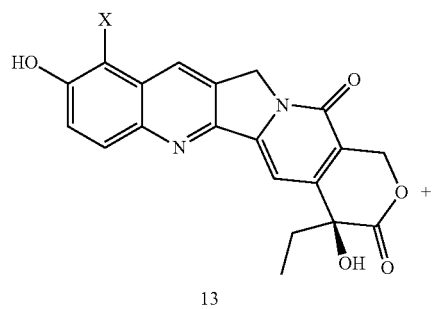

13

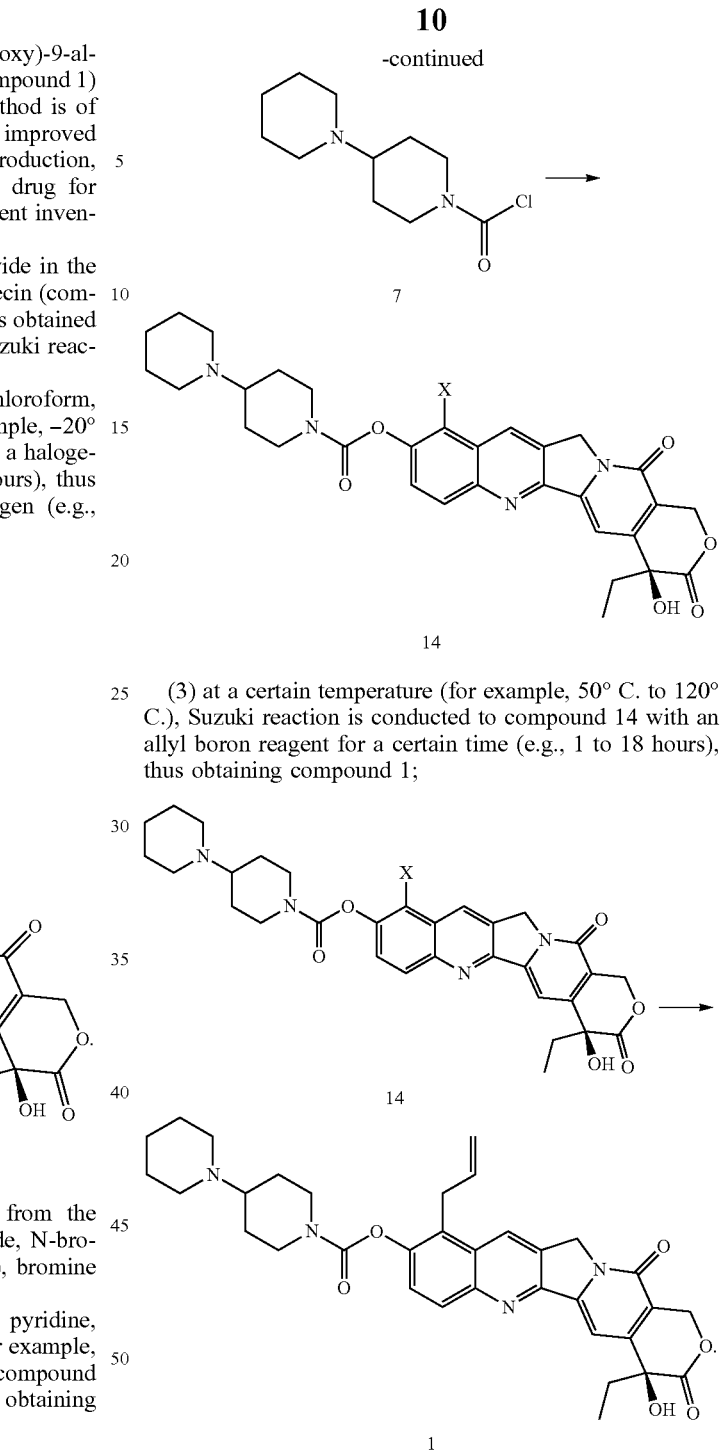

(3) at a certain temperature (for example, $50°$ C. to $120°$ C.), Suzuki reaction is conducted to compound 14 with an allyl boron reagent for a certain time (e.g., 1 to 18 hours), thus obtaining compound 1;

Suzuki reaction is conducted in a system selected from the following group, wherein some of them are experimentally verified, while others can be achieved by experience through simple replacement of reagents according to experience: (1) tris (dibenzylideneacetone) dipalladium, potassium fluoride, tri-tert-butylphosphine and 1,4-dioxane; (2) tris (dibenzylideneacetone) dipalladium, tri-tert-butylphosphine, hydrated potassium phosphate and 1,4-dioxane; (3) tris (dibenzylideneacetone) dipalladium, tri-tert-butylphosphine, potassium carbonate and 1,4-dioxane; (4) tris (dibenzylideneacetone) dipalladium, tri-tert-butylphosphine, hydrated potassium phosphate, potassium fluoride and 1,4-dioxane; (5) tris (dibenzylideneacetone) dipalladium, tritert-butylphosphine, diisopropylethylamine, potassium fluoride and 1,4-dioxane; (6) tris (dibenzylideneacetone) dipalladium, tri-tert-butylphosphine, diisopropylethylamine, cesium fluoride and 1,4-dioxane; (7) tris (dibenzylideneacetone) dipalladium, tri-tert-butylphosphine, triethylamine, potassium fluoride and 1,4-dioxane; (8) tris (dibenzylideneacetone) dipalladium, tri-tert-butylphosphine, triethylamine, potassium fluoride and tetrahydrofuran; (9) tetrakis (triphenylphosphine) palladium, tri-tert-butylphosphine, potassium fluoride and 1,4-dioxane; (10) palladium acetate, tri-tert-butylphosphine, potassium fluoride and 1,4-dioxane; (11) dichlorobis (triphenylphosphine) palladium, tri-tert-butylphosphine, potassium fluoride and 1,4-dioxane; (12) tris (dibenzylideneacetone) dipalladium, tri-tert-butylphosphine, triethylamine, potassium fluoride and methanol; (13) tris (dibenzylideneacetone) dipalladium, tri-tert-butylphosphine, diisopropylethylamine, potassium fluoride and methanol; (14) tris (dibenzylideneacetone) dipalladium, tri-tert-butylphosphine, diisopropylethylamine and methanol; (15) tetrakis (triphenylphosphine) palladium, tri-tert-butylphosphine, diisopropylethylamine and methanol; (16) dichlorobis (triphenylphosphine) palladium, tri-tert-butylphosphine, diisopropylethylamine and methanol; (17) tris (dibenzylideneacetone) dipalladium, triphenylphosphine, diisopropylethylamine, potassium fluoride and isopropanol; (18) tris (dibenzylideneacetone) dipalladium, tri-tert-butylphosphine tetrafluoroborate, diisopropylethylamine and isopropanol; (19) tris (dibenzylideneacetone) dipalladium, tri-tert-butylphosphine, diisopropylethylamine, potassium fluoride, water and isopropanol; (20) tris (dibenzylideneacetone) dipalladium, tri-tert-butylphosphine, diisopropylethylamine, potassium fluoride, water and n-butyl alcohol; (21) dichlorobis (triphenylphosphine) palladium, tri-tert-butylphosphine, diisopropylethylamine, water and n-butyl alcohol; (22) tris (dibenzylideneacetone) dipalladium, tri-tert-butylphosphine, diisopropylethylamine, potassium fluoride and n-butyl alcohol; (23) tris (dibenzylideneacetone) dipalladium, tri-tert-butylphosphine, diisopropylethylamine and n-butyl alcohol; (24) tris (dibenzylideneacetone) dipalladium, potassium fluoride, tri-tert-butylphosphine tetrafluoroborate, diisopropylethylamine, 1,4-dioxane and water; (25) tris (dibenzylideneacetone) dipalladium, potassium fluoride, tri-tert-butylphosphine tetrafluoroborate, diisopropylethylamine, 1,4-dioxane and water; (26) tris (dibenzylideneacetone) dipalladium, potassium fluoride, tri-tert-butylphosphine tetrafluoroborate, diisopropylethylamine, isopropanol and water;

During step (3), after Suzuki reaction is ended, compound 1 can be purified by filtration, column chromatography, and recrystallization.

Moreover, the method can further comprise a step of: acidifying compound 1 to give compound 1H.

1H

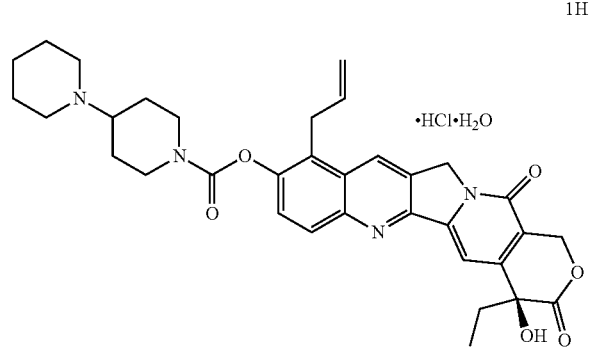 [SMILES: C=CCc1c(OC(=O)N2CCC(N3CCCCC3)CC2)ccc2nc3c(cc12)Cn1c-3cc2c(c1=O)COC(=O)[C@]2(O)CC]

Compared with the prior art, the present invention mainly possesses the following advantages:

1. A novel preparation method for compound 1 is provided. Compared with the currently employed manufacturing processes, the production time of a single batch can be reduced by 50% through the synthesis process of the present invention, thereby greatly improving the production efficiency. Secondly, the total yield has been increased from 16-20% to 70-80%, thereby greatly enhancing the use efficiency of raw materials, and reducing the costs. Finally, the technology has avoided the highly toxic9-allyl-10-hydroxycamptothecin (compound 6) intermediate can be avoided according to the process of the present invention, thus greatly improving the safety of operating person. And the operation process of the present technology is very simple.

2. A method for the preparation of intermediate of compound 1 is further provided.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

Reaction I

Example 1

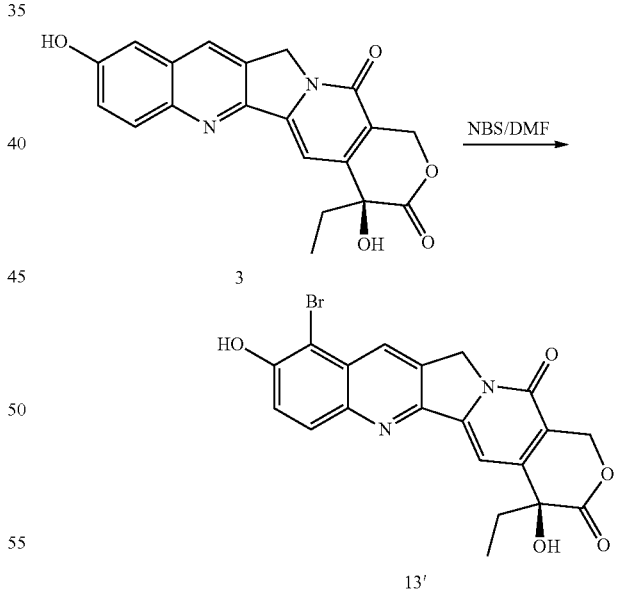

10-hydroxycamptothecin (Compound 3, 20.0 g, 54.95 mmol) was dissolved in DMF (480 mL), and then the internal temperature was reduced to 0° C. in an ice-water bath. N-bromosuccinimide (9.78 g, 54.95 mmol) was added, and reacted under room temperature for 2 h. After the reaction was completed, the reaction mixture was poured into 800 mL of ice water, and pH value was adjusted to 3-4 with 1N HCl. The mixture was thoroughly stirred, filtrated through suction, washed with water, and dried in a blast oven at 40° C. to give 24 g of a yellow solid (Compound 13'), yield of which was 98%.

HNMR (DMSO-d6): δ 0.87 (t, J=7.2 Hz, 3H), 1.82-1.89 (m, 2H), 5.30 (s, 2H), 5.42 (s, 2H), 6.51 (s, 1H), 7.28 (s, 1H), 7.62 (d, J=9.2 Hz, 1H), 8.22 (d, J=9.2, 1H), 8.74 (s, 1H), 11.19 (s, 1H).

Example 2

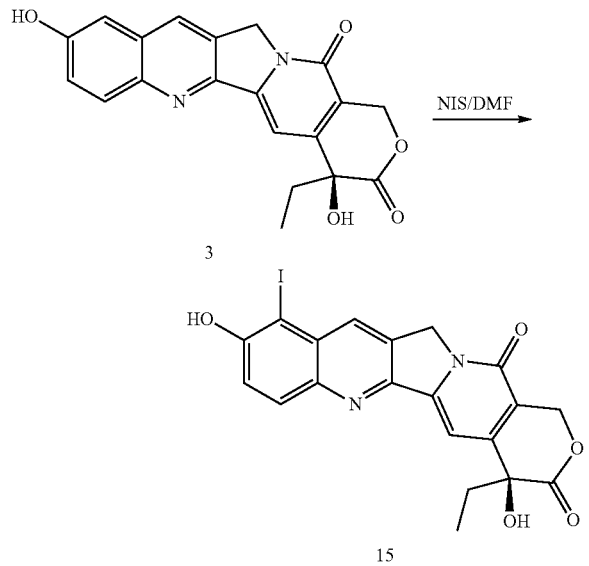 [SMILES: CC[C@@]1(O)C(=O)OCc2c1cc1n(c2=O)Cc2cc3cc(O)ccc3nc2-1 ; CC[C@@]1(O)C(=O)OCc2c1cc1n(c2=O)Cc2cc3c(Br)c(O)ccc3nc2-1]

10-hydroxycamptothecin (Compound 3, 500 mg, 1.37 mmol) was dissolved in DMF (12 mL), and then the internal temperature was reduced to 0° C. in an ice-water bath. N-iodosuccinimide (309 mg, 1.37 mmol) was added, and reacted under room temperature for 2 h. After the reaction was completed, the reaction mixture was poured into 20 mL of ice water, and pH value was adjusted to 3-4 with 1N HCl. The mixture was thoroughly stirred, filtrated through suction, washed with water, and dried in a blast oven at 40° C. to give 730 mg of a yellow solid (Compound 15), yield of which was 97%.

HNMR (DMSO-d6): δ 0.87 (t, J=7.2 Hz, 3H), 1.82-1.89 (m, 2H), 5.31 (s, 2H), 5.42 (s, 2H), 6.53 (s, 1H), 7.28 (s, 1H), 7.57 (d, J=8.8 Hz, 1H), 8.06 (d, J=9.2 Hz, 1H), 8.66 (s, 1H), 11.29 (s, 1H).

Reaction II

Example 3

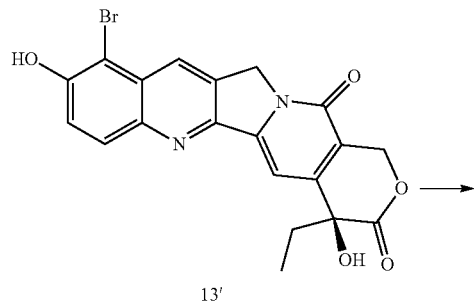

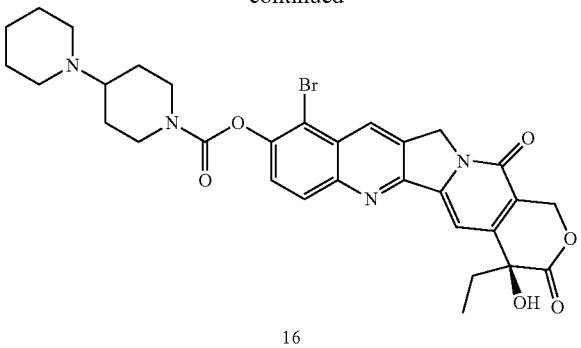

Method for Alkalify 4-Piperidinyl Piperidine Formyl Chloride Hydrochloride Salt:

10% of sodium hydroxide was pre-cooled to room temperature. 4-piperidinyl piperidine formyl chloride hydrochloride salt (23.5 g, 87.92 mmol) was placed in a reaction flask, and methylene chloride (240 mL) was added, and stirred until the solids were uniform dispersed and there was no obvious agglomeration. 10% sodium hydroxide (175 mL) was added, and stirred vigorously for 20 seconds. Layers were quickly separated, the aqueous layer was extracted with dichloromethane (120 mL), and the combined organic layer was washed with a saturated sodium chloride solution, dried over anhydrous sodium sulfate, and filtered. Solids were washed, and the filtrate was dried in vacuo, and transferred into a vial for use.

Compound 13' (24 g, 54.17 mmol) was placed in a reaction flask, and pyridine (300 mL) was added, and stirred slowly at room temperature until dissolved completely. After dissolved completely, the internal temperature was reduced to about −10° C. in an ice-salt bath. Pre-alkalized 4-piperidinyl piperidine carboxylic acid chloride (compound 7, 23.5 g, 87.92 mmol) was dissolved in dichloromethane (50 mL), and transferred into a constant pressure dropping funnel, the reaction solution was slowly added drop wise, and the temperature was controlled to less than −5° C. After the drop wise addition was completed, the reaction liquid was stirred for 2 hours at room temperature. When the reaction was completed, water (240 mL) was added and stirred for 10 min, extracted with dichloromethane (240 mL), the aqueous layer was washed with a saturated sodium carbonate solution (24 mL), then extracted with dichloromethane (240 mL), the organic layers were combined, washed with a saturated sodium chloride solution (300 mL), dried over anhydrous sodium sulfate and dried in vacuo, and pyridine was removed to obtain the product in solid. The solid was then recrystallized in dichloromethane (with 5% isopropanol) (75 mL) and diethyl ether (220 mL), and filtered to collect crystals. The crystals were washed with diethyl ether, and dried under vacuum at 40° C., thereby obtaining about 33 g of product (compound 16) in light yellow solid, yield of which was 95%.

HNMR (DMSO-d6): δ 0.88 (t, J=9.0 Hz, 3H), 1.41-1.63 (m, 9H), 1.81-1.92 (m, 4H), 2.91-2.97 (m, 1H), 3.10-3.16 (m, 1H), 4.05-4.08 (m, 1H), 4.31-4.35 (m, 1H), 5.33 (s, 2H), 5.43 (s, 2H), 6.56 (s, 1H), 7.35 (s, 1H), 7.82 (d, J=8.8 Hz, 1H), 8.22 (d, J=8.8 Hz, 1H), 8.90 (s, 1H).

Example 4

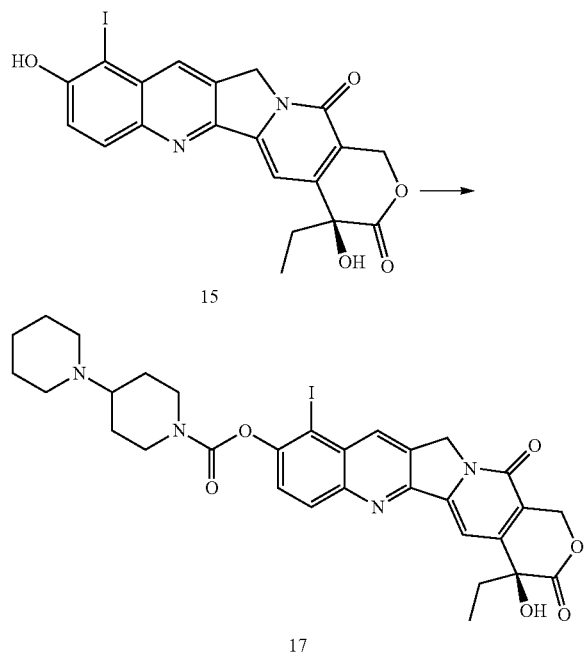

Compound 15' (730 mg, 54.17 mmol) was placed in a reaction flask, and pyridine (10 mL) was added, and stirred slowly at room temperature until dissolved completely. After dissolved completely, the internal temperature was reduced to about −10° C. in an ice-salt bath. Pre-alkalized 4-piperidinyl piperidine carboxylic acid chloride (366 mg, 1.37 mmol) was dissolved in dichloromethane (5 mL), and transferred into a dropping funnel, the reaction solution was slowly added drop wise, and the inner temperature was controlled to less than −5° C. (which requires slowly drop wise addition). After the drop wise addition was completed, the reaction was stirred for 2 hours at room temperature. When the reaction was completed, water (20 mL) was added and stirred for 10 min, extracted with dichloromethane (20 mL), the aqueous layer was washed with a saturated sodium carbonate solution (5 mL), then extracted with dichloromethane, and the organic layers were combined, washed with a saturated sodium chloride (30 mL), dried over anhydrous sodium sulfate and dried in vacuo, and pyridine was removed. The solids were then recrystallized in dichloromethane (with 5% isopropanol) (2 mL) and diethyl ether (6 mL), and filtered, and the crystals were collected, washed with diethyl ether, and dried under vacuum at 40° C. 909 mg of product in light yellow solid was obtained (compound 17), yield of which was 97%.

HNMR (DMSO-d6): δ 0.88 (t, J=7.2 Hz, 3H), 1.41-1.66 (m, 9H), 1.82-1.92 (m, 4H), 2.90-2.97 (m, 1H), 3.10-3.16 (m, 1H), 4.06-4.09 (m, 1H), 4.35-4.38 (m, 1H), 5.35 (s, 2H), 5.44 (s, 2H), 6.56 (s, 1H), 7.36 (s, 1H), 7.73-7.76 (d, J=8.8 Hz, 1H), 8.18-8.21 (d, J=8.8 Hz, 1H), 8.83 (s, 1H).

Reaction III

Example 5

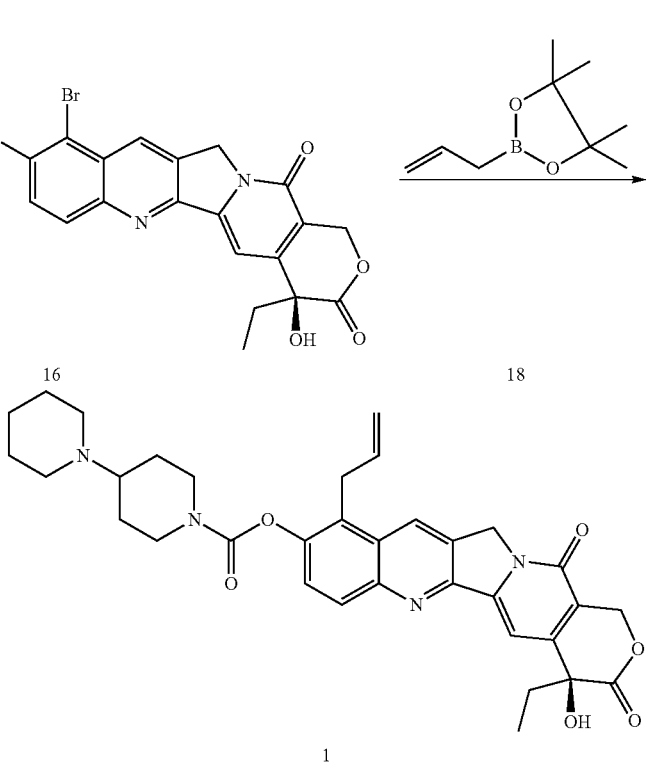

Compound 16 (2500 mg, 3.925 mmol), Pd$_2$(dba)$_3$ (359 mg, 0.392 mmol), tri-tert-butylphosphine tetrafluoroborate (273 mg, 0.942 mmol) and KF (6829 mg, 117.739 mmol) were placed in a 250 mL three-necked reaction flask. Under the protection of nitrogen, 1,4-dioxane (150 mL) was added at room temperature, and stirred to homogeneously dispersed in the system. Under room temperature, DIPEA (1519 mg, 11.774 mmol) and H₂O (7064 mg, 392.465 mmol) were added and stirred to uniform, allyl boronic acid pinacol ester 18 (6593 mg, 39.246 mmol) was added, stirred to uniform, then heated to 60° C. for 2.5 h. After the reaction was completed, 20 ml of dichloromethane was added, filtered through Celite, and washed with 30 mL of dichloromethane, and the solvent was dried in vacuo, purified through column chromatography (dichloromethane: methanol=50:1-15:1) to obtain a yellow solid (compound 1) 2.2 g, yield of which was 88%.

HNMR (DMSO-d6): δ 0.89 (t, J=7.5 Hz, 3H), 1.37-1.39 (m, 1H), 1.67-1.93 (m, 9H), 2.17-2.23 (m, 2H), 2.87-2.93 (m, 3H), 3.09-3.13 (m, 1H), 3.35-3.41 (m, 3H), 3.81 (d, J=6.0 Hz, 2H), 4.16-4.18 (m, 1H), 4.38-4.40 (m, 1H), 5.01-5.07 (m, 2H), 5.27 (s, 2H), 5.43 (s, 2H), 5.96-6.04 (m, 1H), 6.53 (s, 1H), 7.33 (s, 1H), 7.68 (d, J=9.0 Hz, 1H), 8.08 (d, J=9.0 Hz, 1H), 8.87 (s, 1H), 10.72 (s, 1H).

Example 6

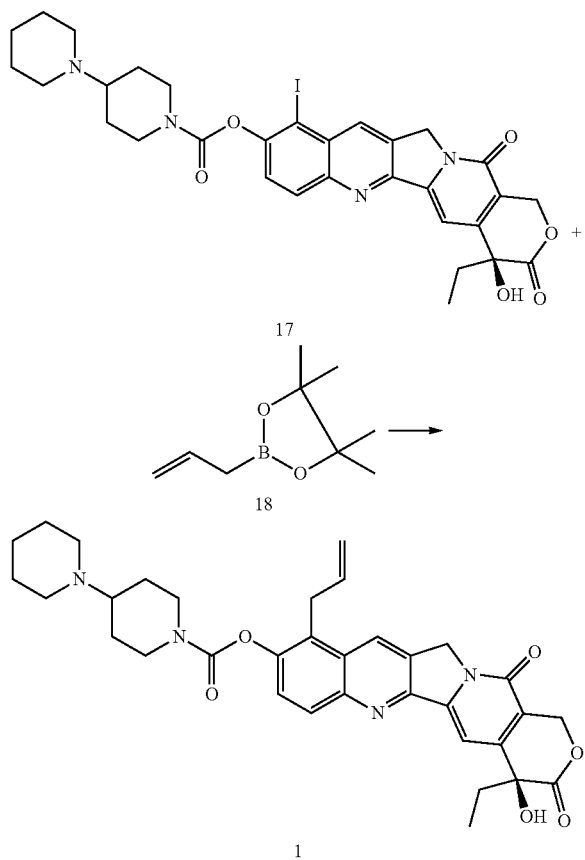

Compound 17 (100 mg, 0.146 mmol), Pd₂(dba)₃ (14 mg, 0.014 mmol), tri-tert-butylphosphine tetrafluoroborate (8 mg, 0.015 mmol), KF (8 mg, 0.146 mmol), and potassium phosphate trihydrate (116 mg, 0.438 mmol) were placed in a 50 mL three-necked reaction flask. Under the protection of nitrogen, 1,4-dioxane (6 mL) was added at room temperature, stirred to homogeneously dispersed in the system. At room temperature, DIPEA (30 mg, 0.233 mmol) and H₂O (28.3 mg, 1.570 mmol) were added and stirred to uniform, and allyl boronic acid pinacol ester 18 (28 mg, 0.160 mmol) was added, stirred to uniform, and then heated to 60° C. for 2.5 h. After the reaction was completed, 10 ml of dichloromethane was added and filtered through Celite, the filter cake was washed with 10 mL of dichloromethane, the solvent was dried in vacuo, and the residue was purified through column chromatography (dichloromethane: methanol=50:1-15:1) to obtain 35 mg of a yellow solid (compound 1), yield of which was 40%. NMR data was identical with those in Example 5.

Example 7

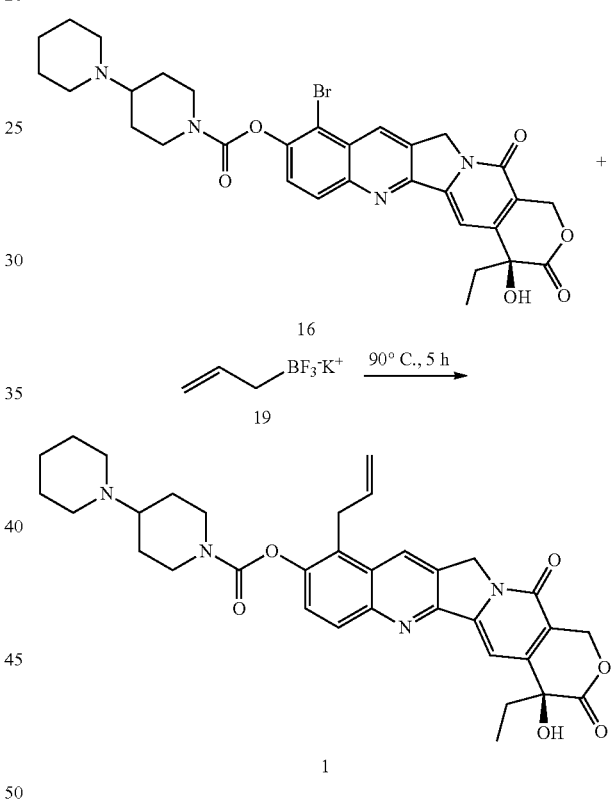

Compound 16 (1000 mg, 1.57 mmol), compound 19 (2320 mg, 15.7 mmol), Pd₂(dba)₃ (140 mg, 0.16 mmol), tri-tert-butylphosphine tetrafluoroborate (110 mg, 0.24 mmol) and KF (2731 mg, 47.1 mmol) were placed in a 100 mL three-necked reaction flask. Under the protection of nitrogen, isopropanol (60 mL) was added at room temperature and stirred. DIPEA (608 mg, 4.71 mmol) and H₂O (700 mg, 39 mmol) were then added, stirred and heated to 90° C. for 5 h. After the reaction was completed, 100 ml of dichloromethane was added and filtered through Celite, washed with 100 mL of dichloromethane, the solvent was dried in vacuo, and the residue was purified through column chromatography (dichloromethane: methanol=50:1-15:1) to obtain 750 mg of a yellow solid, yield of which was 80%. NMR data was identical with those in Example 5.

Compound 1 can also be obtained according to the following conditions from compound 16 or compound 17:

(1) tris (dibenzylideneacetone) dipalladium, potassium fluoride, tri-tert-butylphosphine and 1,4-dioxane;

(2) tris (dibenzylideneacetone) dipalladium, tri-tert-butylphosphine, hydrated potassium phosphate and 1,4-dioxane;

(3) tris (dibenzylideneacetone) dipalladium, tri-tert-butylphosphine, potassium carbonate and 1,4-dioxane;

(4) tris (dibenzylideneacetone) dipalladium, tri-tert-butylphosphine, hydrated potassium phosphate, potassium fluoride and 1,4-dioxane;

(5) tris (dibenzylideneacetone) dipalladium, tri-tert-butylphosphine, diisopropylethylamine, potassium fluoride and 1,4-dioxane;

(6) tris (dibenzylideneacetone) dipalladium, tri-tert-butylphosphine, diisopropylethylamine, cesium fluoride and 1,4-dioxane;

(7) tris (dibenzylideneacetone) dipalladium, tri-tert-butylphosphine, triethylamine, potassium fluoride and 1,4-dioxane;

(8) tris (dibenzylideneacetone) dipalladium, tri-tert-butylphosphine, triethylamine, potassium fluoride and tetrahydrofuran;

(9) tetrakis (triphenylphosphine) palladium, tri-tert-butylphosphine, potassium fluoride and 1,4-dioxane;

(10) palladium acetate, tri-tert-butylphosphine, potassium fluoride and 1,4-dioxane;

(11) dichlorobis (triphenylphosphine) palladium, tri-tert-butylphosphine, potassium fluoride and 1,4-dioxane;

(12) tris (dibenzylideneacetone) dipalladium, tri-tert-butylphosphine, triethylamine, potassium fluoride and methanol;

(13) tris (dibenzylideneacetone) dipalladium, tri-tert-butylphosphine, diisopropylethylamine, potassium fluoride and methanol;

(14) tris (dibenzylideneacetone) dipalladium, tri-tert-butylphosphine, diisopropylethylamine and methanol;

(15) tetrakis (triphenylphosphine) palladium, tri-tert-butylphosphine, diisopropylethylamine and methanol;

(16) dichlorobis (triphenylphosphine) palladium, tri-tert-butylphosphine, diisopropylethylamine and methanol;

(17) tris (dibenzylideneacetone) dipalladium, triphenylphosphine, diisopropylethylamine, potassium fluoride and isopropanol;

(18) tris (dibenzylideneacetone) dipalladium, tri-tert-butylphosphine tetrafluoroborate, diisopropylethylamine and isopropanol;

(19) tris (dibenzylideneacetone) dipalladium, tri-tert-butylphosphine, diisopropylethylamine, potassium fluoride, water and isopropanol;

(20) tris (dibenzylideneacetone) dipalladium, tri-tert-butylphosphine, diisopropylethylamine, potassium fluoride, water and n-butyl alcohol;

(21) dichlorobis (triphenylphosphine) palladium, tri-tert-butylphosphine, diisopropylethylamine, water and n-butyl alcohol;

(22) tris (dibenzylideneacetone) dipalladium, tri-tert-butylphosphine, diisopropylethylamine, potassium fluoride and n-butyl alcohol;

(23) tris (dibenzylideneacetone) dipalladium, tri-tert-butylphosphine, diisopropylethylamine and n-butyl alcohol;

Reaction IV

Example 8

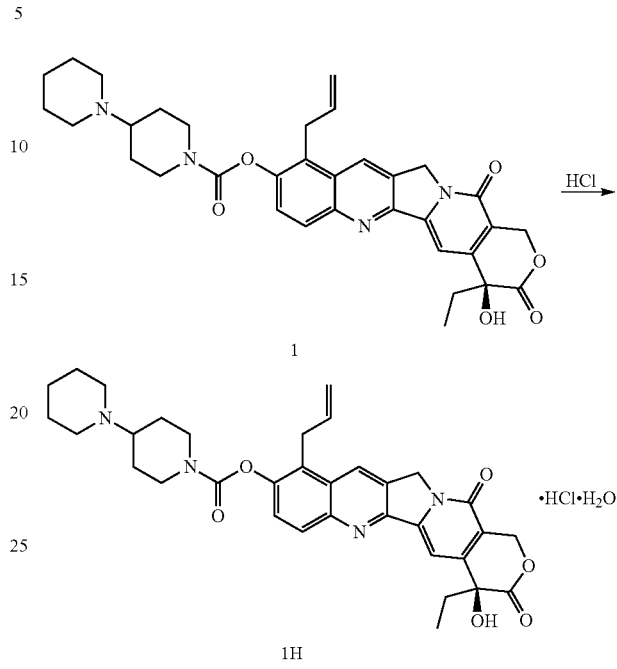

Compound 1 (5 g) was dissolved in dichloromethane (with 5% isopropanol), stirred and cooled to lower than 10° C. 4 M hydrochloric acid in isopropanol was added drop wise to pH=3~5. The internal temperature was raised to room temperature and stirred for 30 minutes. Diethyl ether was added drop wise, and after the addition, it was stirred for 1 hour to give a yellow solid. After filtration, the filter cake was rinsed with ether and dried under vacuum at 35° C., and about 5.8 g of yellow solid was obtained.

The above dried solid was added (11 mL) of water and dissolved. Acetone (88 mL) was added drop wise under reflux, and crystals precipitated upon naturally cooling and precipitated at −10° C. overnight. Crystals were filtered at the next day, washed with acetone and dried to give 4.8 g of solids. The solid was re-dissolved in water (10 mL), and acetone (85 mL) was added drop wise under reflux. Crystals precipitated upon naturally cooling, and precipitated at −10° C. overnight. Crystals were filtered on the next day to give compound 1H in light yellow or white solid (3.5 g).

HNMR (DMSO-d6): δ 0.88 (t, J=7.6 Hz, 3H), 1.40-1.43 (m, 1H), 1.70-1.93 (m, 9H), 2.18-2.25 (m, 2H), 2.93-2.99 (m, 3H), 3.12-3.16 (m, 1H), 3.35-3.42 (m, 3H), 3.80-3.81 (d, J=5.6 Hz, 2H), 4.15-4.18 (m, 1H), 4.37-4.40 (m, 1H), 5.00-5.06 (m, 2H), 5.27 (s, 2H), 5.43 (s, 2H), 5.96-6.03 (m, 1H), 6.55 (s, 1H), 7.33 (s, 1H), 7.66-7.68 (d, J=9.0 Hz, 1H), 8.07-8.09 (d, J=9.0 Hz, 1H), 8.87 (s, 1H), 10.62 (s, 1H)

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound of formula 14,

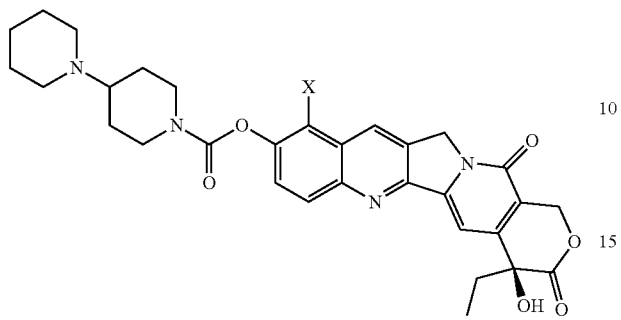

wherein X is a halogen.

2. A preparation method for compound 14, comprising a step: in an inert solvent, reacting compound 13 with compound 7 to give compound 14;

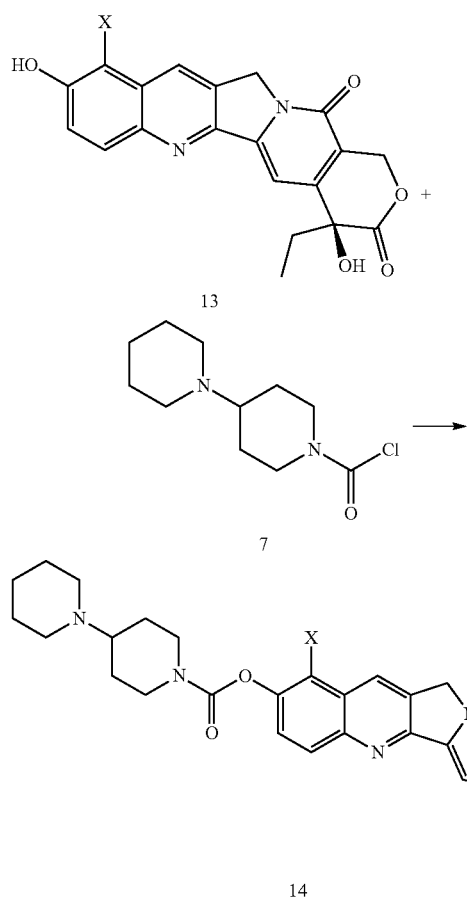

wherein in the above formulas, X is a halogen.

3. The preparation method of claim 2, wherein the compound of formula 13 was prepared by a method comprising the following step:

In an inert solvent, reacting compound 3 with a halogenating agent to give compound 13;

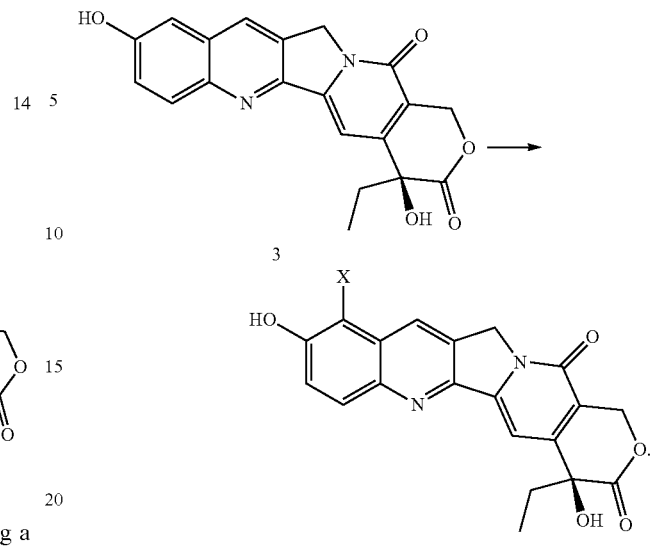

4. A preparation method for compound 1, comprising a step:

conducting Suzuki reaction to compound 14 and an allyl boron reagent to give compound 1;

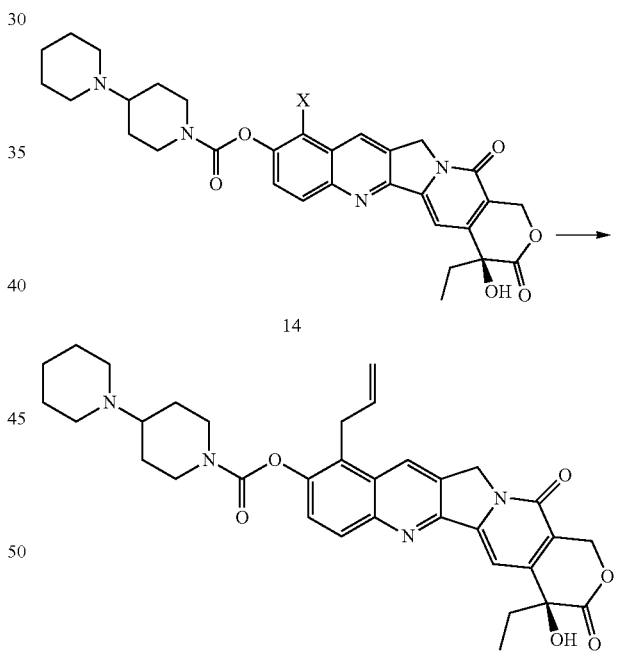

wherein in the above formulas; X is halogen.

5. The preparation method of claim 4; wherein the allyl boron reagent is selected from a group consisting of: allylboronic acid pinacol ester, allyl boron fluoride complex salt.

6. The method of claim 4, wherein the compound of formula 14 as prepared by the method of claim 2.

7. The preparation method of claim 4, wherein Suzuki reaction is conducted in a system comprising the following agents: palladium catalyst, phosphine ligand, alkali and inert solvent.

8. The preparation method of claim 7, wherein,
the palladium catalyst is selected from the group consisting of: tris (dibenzylideneacetone) dipalladium ($Pd_2(dba)_3$); tetrakis (triphenylphosphine) palladium (Pd $(PPh_3)_4$), palladium acetate, dichlorobis (triphenylphosphine) palladium, palladium trifluoroacetate, triphenylphosphine palladium acetate, bis (tri-o-benzyl phosphine) palladium dichloride, 1,2-bis (diphenylphosphino) ethane dichloride palladium or combinations thereof;
the phosphine ligand is selected from the following group: tri-tert-butylphosphine, tri-tert-butylphosphine tetrafluoroborate, tri-n-butylphosphine; tri no tri-p-benzyl phosphine, tricyclohexylphosphine, tri-o-benzyl phosphine, or combinations thereof; the base is selected from the following group: potassium fluoride; cesium fluoride; hydrated potassium phosphate, potassium carbonate, sodium carbonate, sodium hydrogencarbonate, 1,8-diazabicyclo[5.4.0]undec-7-ene, triethylamine, diisopropylethyl amine, pyridine or combinations thereof; the inert solvent is selected from the group: 1,4-dioxane, tetrahydrofuran, acetonitrile, dimethylsulfoxide, N,N-dimethylfornamide, toluene, methanol, ethanol, isopropanol, n-butyl alcohol, t-butanol, isobutanol, benzyl alcohol, water or combinations thereof.

9. The preparation method of claim 4, wherein,
the palladium catalyst is selected from the group consisting of: tris (dibenzylideneacetone) di palladium ($Pd_2(dba)_3$), tetrakis (triphenylphosphine) palladium (Pd $(PPh_3)_4$), or the combinations thereof; the phosphine ligand selected from the group: tri-tert-butylphosphine, tri-tert-butylphosphine tetrafluoroborate, or a combination thereof; and/or
the base is selected from the following group: potassium fluoride, cesium fluoride, potassium phosphate hydrate, diisopropylethylamine, triethylamine, or combinations thereof; the inert solvent is selected from the following group: 1,4-dioxane, isopropanol, water; benzyl alcohol, or combinations thereof.

10. The preparation method of claim 4, wherein the method further comprises the following step: acidizing compound 1 to give compound 1H.

11. The preparation method of claim 4, wherein the allyl boron fluoride complex salt is selected from the following group: the complex salt of allyl boron trifluoride and potassium fluoride.

12. The preparation method of claim 4, wherein the Suzuki reaction is conducted in a system selected from the following group:
(1) tris (dibenzylideneacetone) dipalladium, potassium fluoride, tri-tert-butylphosphine and 1,4-dioxane;
(2) tris (dibenzylideneacetone) dipalladium, tri-tert-butylphosphine, hydrated potassium phosphate and 1,4-dioxane;
(3) tris (dibenzylideneacetone) dipalladium, tri-tert-butylphosphine, potassium carbonate and 1,4-dioxane;
(4) tris (dibenzylideneacetone) dipalladium, tri-tert-butylphosphine, hydrated potassium phosphate, potassium fluoride and 1,4-dioxane;
(5) tris (dibenzylideneacetone) dipalladium, tri-tert-butylphosphine, diisopropylethylamine, potassium fluoride and 1,4-dioxane;
(6) tris (dibenzylideneacetone) dipalladium, tri-tert-butylphosphine, diisopropylethylamine, cesium fluoride and 1,4-dioxane;
(7) tris (dibenzylideneacetone) dipalladium, tri-tert-butylphosphine, triethylamine, potassium fluoride and 1,4-dioxane;
(8) tris (dibenzylideneacetone) dipalladium, tri-tert-butylphosphine, triethylamine, potassium fluoride and tetrahydrofuran;
(9) tetrakis (triphenylphosphine) palladium; tri-tert-butylphosphine, potassium fluoride and 1,4-dioxane;
(10) palladium acetate, tri-tert-butylphosphine, potassium fluoride and 1,4-dioxane;
(11) dichlorobis (triphenylphosphine) palladium, tri-tert-butylphosphine, potassium fluoride and 1,4-dioxane;
(12) tris (dibenzylideneacetone) dipalladium, tri-tert-butylphosphine, triethylamine, potassium fluoride and methanol;
(13) tris (dibenzylideneacetone) dipalladium, tri-tert-butylphosphine, diisopropylethylamine, potassium fluoride and methanol;
(14) tris (dibenzylideneacetone) dipalladium, tri-tert-butylphosphine, diisopropylethylamine and methanol;
(15) tetrakis (triphenylphosphine) palladium, tri-tert-butylphosphine, diisopropylethylamine and methanol;
(16) dichlorobis (triphenylphosphine) palladium, tri-tert-butylphosphine, diisopropylethylamine and methanol;
(17) tris (dibenzylideneacetone) dipalladium, triphenylphosphine, di isopropylethylamine, potassium fluoride and isopropanol;
(18) tris (dibenzylideneacetone) dipalladium, tri-tert-butylphosphine tetrafluoroborate, diisopropylethylamine and isopropanol;
(19) tris (dibenzylideneacetone) dipalladium, tri-tert-butylphosphine, diisopropylethylamine, potassium fluoride, water and isopropanol;
(20) tris (dibenzylideneacetone) dipalladium, tri-tert-butylphosphine, diisopropylethylamine, potassium fluoride, water and n-butyl alcohol;
(21) dichlorobis (triphenylphosphine) palladium, tri-tert-butylphosphine, diisopropylethylamine, water and n-butyl alcohol;
(22) tris (dibenzylideneacetone) dipalladium, tri-tert-butylphosphine, diisopropylethylamine, potassium fluoride and n-butyl alcohol;
(23) tris (dibenzylideneacetone) dipalladium, tri-tert-butylphosphine, diisopropylethylamine and n-butyl alcohol;
(24) tris (dibenzylideneacetone) dipalladium, potassium fluoride, tri-tert-butylphosphine tetrafluoroborate, diisopropylethylamine, 1,4-dioxane and water;
(25) tris (dibenzylideneacetone) dipalladium, potassium fluoride, tri-tert-butylphosphine tetrafluoroborate, diisopropylethylamine, 1,4-dioxane and water;
(26) tris (dibenzylideneacetone) dipalladium, potassium fluoride, tri-tert-butylphosphine tetrafluoroborate, diisopropylethylamine, isopropanol and water.

* * * * *